(12) United States Patent
Leban et al.

(10) Patent No.: US 7,365,094 B2
(45) Date of Patent: Apr. 29, 2008

(54) COMPOUNDS AS ANTI-INFLAMMATORY, IMMUNOMODULATORY AND ANTI-PROLIFERATORY AGENTS

(75) Inventors: Johann Leban, Germering (DE); Stefan Tasler, Gilching (DE)

(73) Assignee: 4SC AG (DE)

( * ) Notice: Subject to any disclaimer, the term of this patent is extended or adjusted under 35 U.S.C. 154(b) by 678 days.

(21) Appl. No.: 10/736,742

(22) Filed: Dec. 17, 2003

(65) Prior Publication Data
US 2004/0192758 A1  Sep. 30, 2004

Related U.S. Application Data

(60) Provisional application No. 60/435,258, filed on Dec. 23, 2002.

(51) Int. Cl.
*A61K 31/341* (2006.01)
*A61K 31/381* (2006.01)
*A61K 31/4025* (2006.01)
*C07D 207/333* (2006.01)
*C07D 307/40* (2006.01)
*C07D 333/26* (2006.01)

(52) U.S. Cl. ............ 514/444; 514/423; 514/448; 514/471; 548/530; 549/59; 549/70; 549/73; 549/483; 549/491

(58) Field of Classification Search ............ 549/59, 549/70, 72, 483, 491; 514/444, 448, 471; 514/423; 548/530
See application file for complete search history.

(56) References Cited

U.S. PATENT DOCUMENTS

| 3,465,001 | A |   | 9/1969 | Bolhofer et al. |
|---|---|---|---|---|
| 4,126,691 | A |   | 11/1978 | Carney et al. |
| 4,661,630 | A |   | 4/1987 | Harigaya et al. |
| 5,258,357 | A | * | 11/1993 | Muenster et al. ........... 504/193 |
| 5,262,537 | A |   | 11/1993 | Huang et al. |
| 5,886,033 | A |   | 3/1999 | Schwab et al. |
| 6,747,041 | B1 | * | 6/2004 | Katsuhira et al. ........... 514/307 |

FOREIGN PATENT DOCUMENTS

| DE | 28 51 379 | 5/1979 |
|---|---|---|
| DE | 29 21 002 | 11/1979 |
| DE | 33 46 814 | 6/1984 |
| DE | 35 21 303 | 10/1985 |
| DE | 39 33 573 | 4/1991 |
| DE | 195 39 638 | 4/1997 |
| EP | 0 097 056 | 12/1983 |
| EP | 0 337 263 | 10/1989 |
| EP | 0 418 667 | 3/1991 |
| EP | 0 419 944 | 4/1991 |
| EP | 0 440 503 | 8/1991 |
| EP | 0 463 444 | 1/1992 |
| EP | 0 503 410 | 9/1992 |
| EP | 0 573 318 | 12/1993 |
| GB | 2 158 440 | 11/1985 |
| JP | 2-22650 | 1/1990 |
| WO | WO 98/57937 | 12/1998 |
| WO | WO 99/65867 | 12/1999 |
| WO | WO 01/21160 | 3/2001 |
| WO | WO 01/24785 | 4/2001 |
| WO | WO 02/38153 | 5/2002 |
| WO | WO 02/100851 | 12/2002 |
| WO | WO 03/006424 | 1/2003 |
| WO | WO 03/006425 | 1/2003 |
| WO | WO 03/006443 | 1/2003 |

OTHER PUBLICATIONS

E. Kita, et al., Polish Journal of Chemistry, vol. 53, No. 6, pp. 1211-1219, "Protolytic Equilibriums of 4-Pyridoxyl-4, 5, 6, 7-Tetrahydropyrido-[3, 4C] Imidazole and Its Derivatives", 1979 (submitting Chemical Abstracts only, AN 1979: 592609).
F. Thorstensson, et al., Journal of Medicinal Chemistry, vol. 46, No. 7, XP-002274167, pp. 1165-1179, "Synthesis of Novel Thrombin Inhibitors. Use of Ring-Closing Metathesis Reactions for Synthesis of P2 Cyclopentene- and Cyclohexenedicarboxylic Acid Derivatives", 2003.
S.-F. Chen, et al., Biochemical Pharmacology, vol. 40, No. 4, XP-000900094, pp. 709-714, "Structure-Activity Relationship of Quinoline Carboxylic Acids. A New Class of Inhibitors of Dihydroorotate Dehydrogenase", 1990.
J. V. De Julian-Ortiz, et al., Journal of Medicinal Chemistry, vol. 42, XP-002199074, pp. 3308-3314, "Virtual Combinatorial Syntheses and Computational Screening of New Potential Anti-Herpes Compounds", 1999.
Takeda Chemical Industries, et al., Chemical Abstracts+Indexes, vol. 94, No. 25, XP-002199076, 1 page, "Tetrahydrophthalamide Derivatives", Jun. 22, 1981.
Matsui, et al., Chemical Abstracts+Indexes, vol. 84, No. 5, XP-002199075, 1 page, "N-Substituted-Δ'-Cyclopentene-1, 2-Dicarboxylic Acid Monoamides As Herbicides", Feb. 2, 1976.
E. Campaigne, et al., J. Med. Chem., vol. 12, No. 2, XP-002278920, pp. 339-342, "Synthesis of Some Ureidodihydrofurans and Related Pyrimidones as Potential Antimalarials", 1969.

(Continued)

*Primary Examiner*—Kamal A. Saeed
*Assistant Examiner*—Janet L. Coppins
(74) *Attorney, Agent, or Firm*—Womble Carlyle Sandridge & Rice, PLLC; Mark D. Jenkins, Esq.

(57) ABSTRACT

The present invention relates to compounds of the general formula (II) and salts and physiologically functional derivatives thereof,

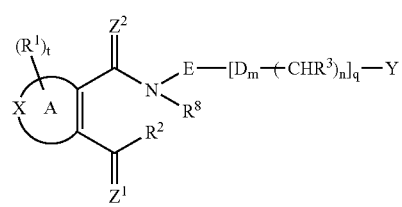

for the use as a medicament.

7 Claims, No Drawings

OTHER PUBLICATIONS

T. Trnovec, et al., Die Pharmazie, vol. 40, No. 6, XP-002275746, pp. 410-411, "Pharmacokinetics of Ethimizol in Man", Jun. 1985.

W. Küster, et al., Berichte Der Deutschen Chemischen Gesellschaft, vol. 57, No. 3, XP-002275747, pp. 409-413, "Über Die Bildung Von Pyrrol-Derivaten Aus Amined Von Beta-Diketonsäure-Estern.", Mar. 12, 1924.

N. Yasuda, Journal of Heterocyclic Chemistry, vol. 22, XP-002275748, pp. 413-416, "Synthesis of Novel Imidazole-4, 5-Dicarboxylic Acid Derivatives", 1985.

A. J. Carpenter, et al., Journal of Organic Chemistry, vol. 50, No. 22, XP-002275749, pp. 4362-4368, "The Scope and Limitations of Carboxamide-Induced β-Directed Metalation of 2-Substituted Furan, Thiophene, and 1-Methylpyrrole Derivatives. Application of the Method to Syntheses of 2, 3-Disubstituted Thiophenes and Furans", Nov. 1, 1985.

* cited by examiner

COMPOUNDS AS ANTI-INFLAMMATORY, IMMUNOMODULATORY AND ANTI-PROLIFERATORY AGENTS

The present invention relates to novel compounds that can be used as anti inflammatory, immunomodulatory and anti-proliferutory agents. In particular the invention refers to new compounds which inhibit dihydroorotate dehydrogenase (DHODH), a process for their manufacture, pharmaceutical compositions containing them and to their use for the treatment and prevention of diseases, in particular their use in diseases where there is an advantage in inhibiting dihydroorotate dehydrogenase (DHODH).

Rheumatoid arthritis (RA) is a disease which is quite common especially among elder people. Its treatment with usual medications as for example non-steroid anti-inflammatory agents is not satisfactory. In view of the increasing ageing of the population, especially in the developed Western countries or in Japan the development of new medications for the treatment of RA is urgently required.

WO 99/38846 and EP 0 646 578 disclose compounds which are reported to be useful for treatment of RA.

A medicament against rheumatoid arthritis with a new mechanism of action, leflunomide, was recently put on the market by the company Aventis under the tradename ARAVA [EP 780128, WO 97/34600]. Leflunomide has immunomodulatory as well as anti-inflammatory properties [EP 217206, DE 2524929]. The mechanism of action is based upon the inhibition of dihydroorotate dehydrogenase (DHODH), an enzyme of the pyrimidine biosynthesis.

In the body, DHODH catalyzes the synthesis of pyrimidines, which are necessary for cell growth. An inhibition of DHODH inhibits the growth of (pathologically) fast proliferating cells, whereas cells which grow at normal speed may obtain their required pyrimidine bases from the normal metabolic cycle. The most important types of cells for the immuno response, the lymphocytes, use exclusively the synthesis of pyrimidines for their growth and react particularly sensitively to DHODH inhibition. Substances that inhibit the growth of lymphocytes are important medicaments for the treatment of auto-immuno diseases.

The DHODH inhibiting leflunomide (ARAVA) is the first medicament of this class of compounds (leflunomides) for the treatment of rheumatoid arthritis. WO 99/45926 is a flier reference that discloses compounds which act as inhibitors of DHODH.

In EP 463444, WO 98/57937, EP 150034, Nucleosides & Nucleotides 1997, 16 (10 & 11), 2025-2033, Egyptian Journal of Pharmaceutical Sciences 1991, 32 (1-2), 331-339, Journal für Praktische Chemie 1991, 333 (4), 619-624, Archives of Pharmacal Research 1990, 13 (4), 338-341, Sulfur Letters 1988, 7 (4), 127-136, Synthesis 1988, 6 449-452, Sulfur Letters 1987, 7 (19), 19-24, Archiv der Pharmazie 1987, 320 (12), 1281-1283, Natl. Def. Med. Cent. 1983, 35 (1), 57-64 and Sch. Pharm. Sci. 1977, 97 (4), 410-415 a number of five membered aromatic ring systems fused to substituted maleimide are described.

It is an object of the present invention to provide alternative effective agents which can be used for the treatment of diseases which require the inhibition of DHODH.

Accordingly, a novel class of compounds with an inhibitory effect on DHODH, in particular human DHODH, was found.

The present invention is also directed to compounds of the general formula (II)

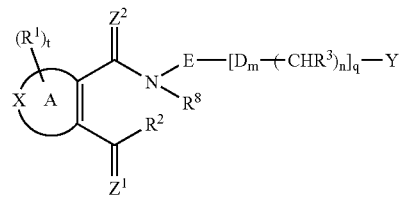

wherein

A is a heteroaromatic 5-membered ring system containing one or more groups X selected from the group consisting of S, O, N, $NR^4$, $SO_2$ and SO;

D is O, S, $SO_2$, $N^4$, or $CH_2$;

$Z^1$ and $Z^2$ are independent from each other O, S, or $NR^5$;

$R^1$ independently represents H, halogen, haloalkyl, haloalkyloxy —$CO_2R''$, —$SO_3H$, —OH, —$CONR*R''$, —$CR''O$, —$SO_2$—$NR*R''$, —$NO_2$, —$SO_2$—$R''$, —SO—$R*$, —CN, alkoxy, alkylthio, aryl, —$NR''$—$CO_2$—$R'$, —$NR''$—CO—$R*$, —$NR''$—$SO_2$—$R'$, —O—CO—$R*$, —O—$CO_2$—$R*$, —O—CO—$NR*R''$; cycloalkyl, alkylamino, hydroxyalkylamino, —SH, heteroaryl, or alkyl;

$R^*$ independently represents H, alkyl, cycloalkyl, an aminoalkyl, alkoxy, —OH, —SH, alkythio, hydroxyalkyl, haloalkyl, haloalkyloxy, aryl or heteroaryl;

$R'$ independently represents H, —$CO_2R''$, —$CONHR''$, —$CR''O$, —$SO_2NR''$, —$NR''$—CO-haloalkyl, —$NO_2$, —$NR''$—$SO_2$-haloalkyl, —$NR''$—$SO_2$-alkyl, —$SO_2$-alkyl, —$NR''$—CO-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkyloxy, aryl, arylalkyl or heteroaryl;

$R''$ independently represents hydrogen, haloalkyl, hydroxyalkyl, alkyl, cycloalkyl, aryl, heteroaryl or aminoalkyl;

$R^2$ is H or $OR^6$, $NHR^7$, $NR^7OR^7$ or $R^2$ together with the nitrogen atom which is attached to $R^8$ form a 5 or 6 membered heterocyclic ring with the proviso that $R^2$ is —[$CH_2$], and $R^8$ is absent;

$R^3$ is H, alkyl cycloalkyl, aryl, alkoxy, O-aryl; O-cycloalkyl, halogen, aminoalkyl, alkylamino, hydroxylamino, hydroxylalkyl, haloalkyloxy, heteroaryl, alkylthio, S-aryl; S-cycloalkyl, arylalkyl, or haloalkyl;

$R^4$ is H, alkyl, cycloalkyl, aryl or heteroaryl;

$R^5$ is H, OH, alkoxy, O-aryl, alkyl or aryl;

$R^6$ is H, alkyl, cycloalkyl, aryl, arylalkyl, heteroaryl, alkylaryl, alkoxyalkyl acylmethyl, (acyloxy)alkyl, non-symmetrical(acyloxy)alkyldiester, or dialkylphosphate;

$R^7$ is H, OH, alkyl, alkoxy, alkoxy, O-aryl, cycloalkyl, or O-cycloalkyl;

$R^8$ is hydrogen, or alkyl;

E is an alkyl or cycloalkyl group or a monocyclic or polycyclic substituted or unsubstituted ring system which may contain one or more groups X and which contain at least one aromatic ring;

Y is hydrogen, halogen, haloalkyl, haloalkyloxy, alkyl, cycloalkyl, a monocyclic or polycyclic substituted or unsubstituted ring system which may contain one or more groups X and which contains at least one aromatic ring or

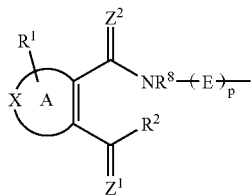

m is 0 or 1;
n is 0 or 1;
p is 0 or 1;
q is 0 or 1;
s is 0 to 2; and
t is 0 to 3;

with the proviso that the following compounds are excluded:
compounds wherein ring A contains five atoms, $Z^1=Z^2=O$, and $R^2$ together with the nitrogen atom which is attached to $R^8$ form a 5 membered heterocyclic ring with the proviso that $R^2$ is —[CH$_2$]$_8$, $R^8$ is absent and s is 0;
compounds wherein ring A contains three carbon atoms and two nitrogen atoms, $Z^1=Z^2=O$, and $R^2$ together with the nitrogen atom which is attached to $R^8$ forms a 5 membered heterocyclic ring with the proviso that $R^2$ is —[CH$_2$]$_8$, $R^8$ is absent and s is 0;
4-[4(naphthalin-2-yl)thiazol-2-ylaminocarbonyl]-furan-3-carboxylic acid; and
5-[4(naphthalin-2-yl)thiazol-2-ylaminocarbonyl]-2H-[1,2,3]-triazole-4-carboxylic acid.

an alkyl group, if not stated otherwise, denotes a linear or branched $C_1$-$C_6$-alkyl, preferably a linear or branched chain of one to five carbon atoms, a linear or branched $C_1$-$C_6$-alkenyl or a linear or branched $C_1$-$C_6$-alkinyl group, which can optionally be substituted by one or more substituents R', preferably by halogen;

the $C_1$-$C_6$-alkyl, $C_1$-$C_6$-alkenyl and $C_1$-$C_6$-alkinyl residue may be selected from the group comprising —CH$_3$, —C$_2$H$_5$, —CH=CH$_2$, —C≡CH, —C$_3$H$_7$, —CH(CH$_3$)$_2$, —CH$_2$—CH=CH$_2$, —C(CH$_3$)=CH$_2$, —CH=CH—CH$_3$, —C≡C—CH$_3$, —CH$_2$—C≡CH, —C$_4$H$_9$, —CH$_2$—CH(CH$_3$)$_2$, —CH(CH$_3$)—C$_2$H$_5$, —C(CH$_3$)$_3$, —C$_5$H$_{11}$, —C$_6$H$_{13}$, —C(R')$_3$, —C$_2$(R')$_5$, —CH$_2$—C(R')$_3$, —C$_3$(R')$_7$, —C$_2$H$_4$—C(R')$_3$, —C$_2$H$_4$—CH=CH$_2$, —CH=CH—C$_2$H$_5$, —CH=C(CH$_3$)$_2$, —CH$_2$—CH=CH—CH$_3$, —CH=CH—CH=CH$_2$, —C$_2$H$_4$—C≡CH, —C≡C—C$_2$H$_5$, —CH$_2$C=C—CH$_3$, —C≡C—CH=CH$_2$, —CH=CH—C=CH, —C≡C—C≡CH, —C$_2$H$_4$—CH(CH$_3$)$_2$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —C$_3$H$_6$—CH=CH$_2$, —CH=CH—C$_3$H$_7$, —C$_2$H$_4$—CH=CH—CH$_3$, —CH$_2$—CH=CH—C$_2$H$_5$, —CH$_2$—CH=CH—CH=CH$_2$, —CH=CH—CH=CH—CH$_3$, —CH=CH—CH$_2$—CH=CH$_2$, —C(CH$_3$)=CH—CH=CH—CH$_2$, —CH=C(CH$_3$)—CH=CH$_2$, —CH=CH—C(CH$_3$)=CH$_2$, —CH$_2$—CH=C(CH$_3$)$_2$, —C(CH$_3$)=C(CH$_3$)$_2$, —C$_3$H$_6$—C≡CH, —C≡C$_3$H$_7$, —C$_2$H$_4$—C≡C—CH$_3$, —CH$_2$—C≡C—C$_2$H$_5$, —CH$_2$—C≡C—CH=CH$_2$, —CH$_2$—CH=CH—C≡CH, —CH$_2$—C≡C—C≡CH, —C≡C—C$_2$H$_4$—CH$_3$, —CH=CH—C≡C—CH$_3$, —C≡C—C≡C—CH$_3$, —C≡C—CH$_2$—CH=CH$_2$, —CH=CH—CH$_2$—C≡CH, —C≡C—CH$_2$—C≡CH, —C(CH$_3$)=CH—CH=CH$_2$, —C(CH$_3$)=CH—CH$_2$, —CH=CH—C(CH$_3$)=CH$_2$, —C(CH$_3$)=CH—C≡CH, —CH=C(CH$_3$)—C≡CH, —C≡C—C(CH$_3$)=CH$_2$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —C$_4$H$_8$—CH=CH$_2$, —CH=CH—C$_4$H$_9$, —C$_3$H$_6$—CH=CH—CH$_3$, —CH$_2$—CH=CH—C$_3$H$_7$, —C$_2$H$_4$—CH=CH—C$_2$H$_5$, —CH$_2$—C(CH$_3$)=C(CH$_3$)$_2$, —C$_2$H$_4$—CH=C(CH$_3$)$_2$, —C$_4$H$_8$—C≡CH, —C≡C—C$_4$H$_9$, —C$_3$H$_6$—C≡C—CH$_3$, —CH$_2$—C≡C—C$_3$H$_7$, —C$_2$H$_4$—C≡C—C$_2$H$_5$;

R' independently represents H, —CO$_2$R", —CONHR", —CR"O, —SO$_2$NR", —NR"—CO-haloalkyl, —NO$_2$, —NR"—SO$_2$-haloalkyl, —NR"—SO$_2$-alkyl, —SO$_2$-alkyl, —NR"—CO-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkyloxy, aryl, arylalkyl or heteroaryl;

R" independently represents hydrogen, haloalkyl, hydroxyalkyl, alkyl, cycloalkyl, aryl, heteroaryl or aminoalkyl;

a cycloalkyl group denotes a non-aromatic ring system containing three to eight carbon atoms, preferably four to eight carbon atoms, wherein one or more of the carbon atoms in the ring can be substituted by a group X, X being as defined above; the $C_3$-$C_8$-cycloalkyl residue may be selected from the group comprising -cyclo-$C_3$H$_5$, -cyclo-$C_4$H$_7$, -cyclo-$C_5$H$_9$, -cyclo-$C_6$H$_{11}$, -cyclo-$C_7$H$_{13}$, -cyclo-$C_8$H$_{15}$;

an alkoxy group denotes an O-alkyl group, the alkyl group being as defined above; the alkoxy group is preferably a methoxy, ethoxy, isopropoxy, t-butoxy or pentoxy group;

an alkylthio group denotes an S-alkyl group, the alkyl group being as defined above, an haloalkyl group denotes an alkyl group which is substituted by one to five halogen atoms, the alkyl group being as defined above; the haloalkyl group is preferably a —C(R$^{10}$)$_3$, —CR$^{10}$(R$^{10'}$)$_2$, —CR$^{10}$(R$^{10'}$)R$^{10"}$, —C$_2$(R$^{10}$)$_5$, —CH$_2$—C(R$^{10}$)$_3$, —CH$_2$—CR$^{10}$(R$^{10'}$)$_2$, —CH$_2$—CR$^{10}$(R$^{10'}$)R$^{10"}$, —C$_3$(R$^{10}$)$_7$ or —C$_2$H$_4$—C(R$^{10}$)$_3$, wherein R$^{10}$, R$^{10'}$, R$^{10"}$ represent F, Cl Br or I, preferably F;

a hydroxyalkyl group denotes an HO-alkyl group, the alkyl group being as defined above;

an haloalkyloxy group denotes an alkoxy group which is substituted by one to five halogen atoms, the alkyl group being as defined above; the haloalkyloxy group is preferably a —OC(R$^{10}$)$_3$, —OCR$^{10}$(R$^{10'}$)$_2$, —OCR$^{10}$(R$^{10'}$)R$^{10"}$, —OC$_2$(R$^{10}$)$_5$, —OCH$_2$—C(R$^{10}$)$_3$, —OCH$_2$—CR$^{10}$(R$^{10'}$)$_2$, —OCH$_2$—CR$^{10}$(R$^{10'}$)R$^{10"}$, —OC$_3$(R$_{10}$)$_7$ or —OC$_2$H$_4$—C(R$^{10}$)$_3$, wherein R$^{10}$, R$^{10'}$, R$^{10"}$ represent F, Cl, Br or I, preferably F;

a hydroxyalkylamino group denotes an (HO-alkyl)$_2$-N— group or HO-alkyl-NH— group, the alkyl group being as defined above;

an alkylamino group denotes an HN-alkyl or N-dialkyl group, the alkyl group being as defined above;

a halogen group is chlorine, bromine, fluorine or iodine, fluorine being preferred;

an aryl group preferably denotes an aromatic group having five to fifteen carbon atoms, which can optionally be substituted by one or more substituents R', where R' is as defined above; the aryl group is preferably a phenyl group, —CH$_2$Ph, —C$_2$H$_4$Ph, —CH=CH—Ph, —C≡C-Ph, -o-C$_6$H$_4$—R', -m-C$_6$H$_4$—R', -p-C$_6$H$_4$—R', -o-CH$_2$—C$_6$H$_4$—R', -m-CH$_2$—C$_6$H$_4$—R', -p-CH$_2$—C$_6$H$_4$—R';

a heteroaryl group denotes a 5-or 6-membered heterocyclic group which contains at least one heteroatom like O, N, S. This heterocyclic group can be fused to another ring. For example, this group can be selected from a thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1-imidazolyl, 2-imidazolyl, 1,2,5-thiadiazol-4-yl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-pyrazinyl, 1-pyrazolyl, 3-pyrazolyl, 4-pyrazolyl, 1H-tetrazol-2-yl, 1H-tetrazol-3-yl, tetrazolyl, indolyl, indolinyl, benzo-[b]-furanyl, benzo[b]thiophenyl, benzimidazolyl, benzothiazolyl, quinazolinyl, quinoxazolinyl, or preferably quinolinyl, tetrahydroquinolinyl, isoquinolinyl, tetrahydroisoquinolinyl group. This heterocyclic group can optionally be substituted by one or more substituents R', where R' is as defined above.

The meaning of E includes alkyl groups optionally substituted by one or more substituents R', wherein alkyl is defined as above or as a cycloalkyl group optionally substituted by one or more substituents R' such as cyclopropyl, cyclobutyl, cyclopentyl, cyclohexyl cycloheptyl, cyclooctyl or carbocyclic aromatic groups such as phenyl, 1-naphthyl, 2-naphthyl, anthracenyl, in particular 1-anthracenyl and 2-anthracenyl, and heterocyclic aromatic groups such as N-imidazolyl, 2-imidazolyl, 2-thienyl, 3-thienyl, 2-furanyl, 3-furanyl, 2-pyridyl, 3-pyridyl, 4-pyridyl, 2-pyrimidyl, 4-pyrimidyl, 2-pyranyl, 3-pyranyl, 4-pyranyl, 3-pyrazolyl, 4-pyrazolyl, 5-pyrazolyl, 2-pyrazinyl, 2-thiazolyl, 4-thiazolyl, 5-thiazolyl, 2-oxazolyl, 4-oxazolyl and 5-oxazolyl. E includes also fused polycyclic aromatic ring systems such as 9H-thioxanthene-10,10-dioxide in which a carbocyclic aromatic ring or heteroaryl ring is fused to one or more other heteroaryl ring.

The invention also provides a pharmaceutical composition comprising a compound of formula (II) including the compounds excluded by the disclaimers, in free form or in the form of pharmaceutically acceptable salts and physiologically functional derivatives, together with a pharmaceutically acceptable diluent or carrier therefore.

The term "physiologically functional derivative" as used herein refers to compounds which are not pharmaceutically active themselves but which are transformed into their pharmaceutical active form in vivo, i.e. in the subject to which the compound is administered. Examples of physiologically functional derivatives are prodrugs such as those described below in the present application.

In another aspect, the present invention also provides a method for the treatment or prophylaxis of a condition where there is an advantage in inhibiting dihydroorotate dehydrogenase (DHODH) which comprises the administration of an effective amount of a compound of formula (II) and physiologically acceptable salts or physiologically functional derivatives thereof.

The invention Is also directed to the use of compounds of the formula (II) and of their pharmacologically tolerable salts or physiologically functional derivatives for the production of a medicament for the prevention and treatment of diseases, where inhibition of the pyrimidine biosynthesis is of benefit.

In addition, the present invention provides methods for preparing the compounds of the invention such as compounds of forumula (II).

The compounds of formula (II) may be obtained via various methods. In preferred embodiments of the invention the following method is used for the synthesis of derivatives of formula (II).

Method 1:

The synthesis of dicarboxylic acid dimethylester is described in WO 02/07655. This dicarboxylic acid dimethyl ester can be substituted on the ring system as described by T. Harrison et, al., Tetrahedron Vol. 45, No.16, 1989, 5247-5262. This dicarboxylic acid dimethyl ester can then be converted into the corresponding acid anhydride.

These anhydrides may then be reacted with the corresponding amines to the desired amides of formula (II). This reaction steps are analog to the reaction steps described in WO 02/07655.

The compounds of formula (II) in each case [r=0] can be synthesized analog to the four methods described in WO 02/07655.

In addition, the present invention provides methods for preparing the desired hydroxamic acides of formula (II).

One method for the synthesis of compounds of formula (II) comprises the conversion of an acid to the corresponding acid chloride and reacting the acid chloride with hydroxylamine (Watanabe et al., 1989, J. Org. Chem., 54, 17, 4088-4097; Shishido et al., 1992, J. Org. Chem, 57, 10, 2876-2883).

Other methods for the preparation of formula (II) are described by Woo et al., 2002, J. Med. Chem. 45, 2877-2885; Knorr et al., 1989, Tetrahedron Lett., 30, 1927-1930, Carpino, 1993, J. Am. Chem. Soc., 115, 4397-4398 and Albericio et.al., 1998, J. Org. Chem., 63, 9678-9683.

Another method for the preparation of compounds of formula (II) is the reaction of the corresponding ester with hydroxylaminee as described by Stowell et al., 1995, J. Med. Chem., 38, 8, 1411-1413.

The synthesis of amides of formula (II) is described by J. Zabicky in "The Chemistry of Amides", in the serial of S. Patai (ed.), "The Chemistry of Functional Groups", John Wiley & Sons, 1975, p. 74-131. Methods for preparing thioamides are described in Houben-Weyl, J. Falbe (ed.), G. Thieme Verlag, vol. E5, p. 1219-59. Methods for preparing sulfamides are described by Caldwell et al, *J. Am. Chem. Soc.* 1944, 66, 1479-82, or by Flynn et al., *Med. Chem. Res.,* 1998, 8, 219-43 and Dziadulewicz et al., *Bioorg. Med. Chem. Lett.* 2001, 11, 5, 705-10.

In addition, the present invention provides methods for prepa compounds of formula (I) wherein A is a heterocyclic ring system. For example 3,4-dicarboxylic acids of thiophene, furan and pyrrole were converted into the corresponding anhydrides and reacted with amines in analogy to DE 3933573 and D. P. Arnold, Aust. J. Chem 44, 1991, 323-330.

3-carboxamide-2-carboxylic acids or 2-carboxamide-3-carboxylic acids of thiophene, furan and pyrrole were synthesized from 3-carboxylic acids or 2-carboxylic acids, respectively, by amidation of the acid group and subsequent directed ortho-metalation in 2-or 3-position, respectively, followed by addition of carbon dioxide as electrophile according to DE 3933573.

Differently 4,5-substituted 2,3-pyrroledicarboxylic esters and acids were prepared according to literature procedures:

a) 1-hydroxy-4,5-dimethyl: from dialkyl acetylenedicarboxylates and butane-2,3-dione monooximes, I. Yavari et al., Synth. Commun. 26, 1996, 4495-4499.

b) 3-hydroxy-4-alkyl or -aryl: from dialkyl acetylenedicarboxylates and amino acid esters, P. Kolar et al., Synth. Commun. 24, 1994, 1887-1893.
c) mixed 4,5-alkyl/aryl: from dialkyl acetylenedicarboxylates and aryl-or benzylhydrazones, J. Barluenga et al., Synthesis, 1975, 642-643.
d) 4-methyl: from N-acetonylphthalimide and diethyl oxalacetate, R. E. Lancaster et al., J. Org. Chem. 23, 1958, 1208-1209.

The pyrrole diester can be converted into the corresponding acids and anhydrides for further amidation reactions or directly transformed into the corresponding mono-hydrazinocarbonyls (M. T. Garcia-Lopez et al., J. Chem. Soc. Perkin Trans., 1978, 483-487). Diethyl 2-alkyl-, -aryl-, or -aminothiazole-4,5-carboxylates were synthesized from diethyl α-halo-β-oxosuccinate and the respective thioamides or thiourea in analogy to W. K. Anderson et al., J. Med. Chem. 27, 1984, 1559-1565; E. H. Huntress et al., J. Am. Chem. Soc. 65, 1943, 2167-2169; L. H. Conover et al., J. Am. Chem. Soc. 72, 1950, 5221-5225; M. Robba et al., Bull. Soc. Chim. Fr., 1969, 1762-1768.

All diesters were converted into the monoamides as described above. Mixtures of regioisomers resulting from the amidation reaction had to be separated.

Aromatic systems containing a sulfur atom within the aromatic framework can be converted into the corresponding S-monooxides or -dioxides by oxidation of the aforementioned heterocycles with m-chlorobenzoic acide, either with or without trifluoroborate etherate being added (N. Furukawa et al., Heterocycles 44, 1997, 61-66).

The invention also provides methods for preparing compounds of formula (II) wherein $R^2$ together with the nitrogen atom which is attached to $R^8$ form a 6 membered heterocylic ring system.

For example diethyl 3-acetyl-2-methylfuran-4,5-dicarboxylate was prepared from acetylated sulphonium methylides and diethyl acetylenedicarboxilate according to Tetrahedron 26, 1970, 4353-4360. The diester was converted into the corresponding anhydride, which was next reacted with an amine as described above to give a mixture of regioisomers for monoamidation product. Upon esterification of the carboxylic acid using dicylcohexylcarbodiimide, 4-dimethylaminopyridine and ethanol in methylene chloride, the two regioisomers were separated, and α-bromination at the acetyl functionality of ethyl 3-acetyl-2-methyl-4-carboxamide-furan-5-carboxylate was achieved either with bromine in methylene chloride or copper dibromide in ethyl acetate in analogy to literature procedures: S. Laufer et al., Arch Pharm. 330, 1997, 307-312; S. K. C. Devi et al., Synth. Commun. 32, 2002, 1523-1528, Final ring closure was achieved using sodium hydride in tetrahydrofuran and the ester was saponified under neutral conditions using phenylthiol potassium flouride in 1-methyl-2-pyrrolidinone (M. K. Nayak et al., Chem. Left., 1998, 297-298).

In the compounds of formula (II), the aromatic ring system A contains 5 carbon atoms. In preferred embodiment, the compounds of the present invention contain two conjugated double bonds. One or more of the carbon atoms in the ring system A can be replaced by a group X, wherein X is selected from the group consisting of S, O, N, $NR^4$, SO, CO or $SO_2$.

In one preferred embodiment, in the compounds of formula (II) the aromatic ring system A is selected from the group consisting of:

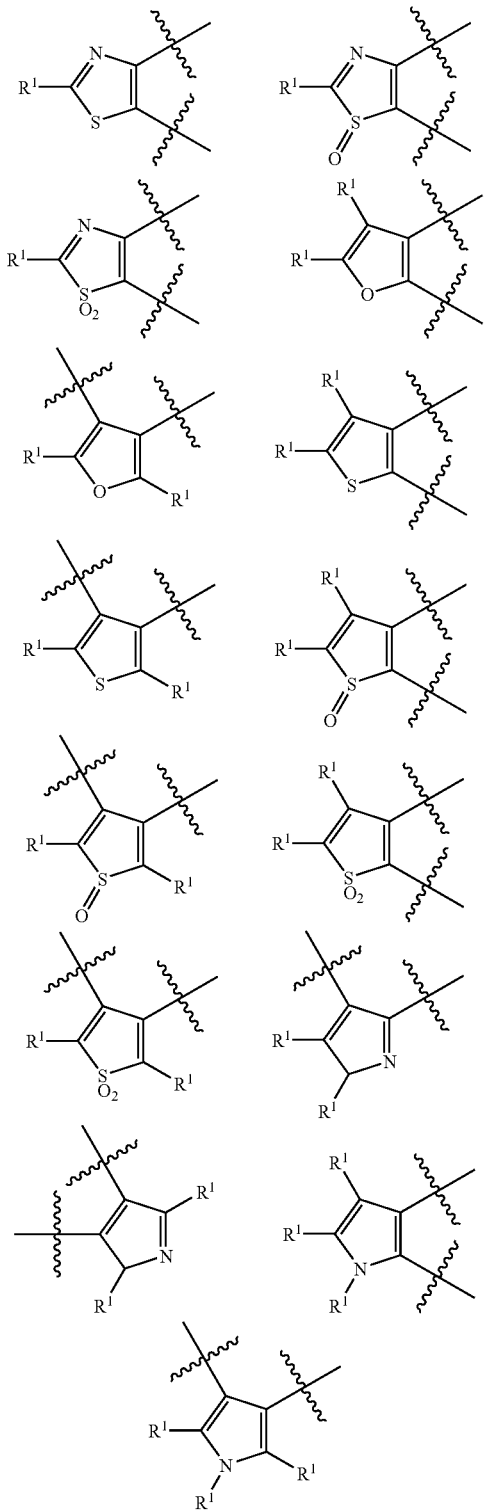

In the compounds of formula (II) $R^1$ is preferably H, OH, $CO_2H$ or $SO_3H$ or tetrazole.

In the compounds of formula (II) $R^2$ is preferably OH, $NH_2$, NHOH, $NHR^7$, $NR^7O^7$ or $OR^6$.

In preferred embodiment, in the compounds of formula (II) $R^6$ is benzoyloxymethyl, isobutyryloxymethyl, 4-aminobutyryloxymethyl, butyryloxymethyl, 1-(butyryloxy)ethyl, 1-(butyryloxy)-2,2-dimethylpropyl, 1-diethylphosphonooxyethyl, 2-(2-methoxyethoxy)-acetyloxymethyl, p-aminobenzoylmethyl, nicotinyloxymethyl, pivaloyloxymethyl, glutaryloxymethyl, [2-(2-methoxyethoxy)ethoxy]-acetyloxymethyl, 2-(morpholine-4-yl)-ethyl, 1-diethyl-phosphonooxymethyl.

In the compounds of formula (II) $R^3$ is H, alkyl, cycloalkyl, aryl, alkoxy, O-aryl; O-cycloalkyl, halogen, aminoalkyl, alkylamino, hydroxylamino, haloalkyl, hydroxylalkyl, haloalkyloxy, heteroaryl, alkylthio, S-aryl; S-cycloalkyl, arylalkyl, preferably H.

In the compounds of formula (II) $R^4$ is H, alkyl, cycloalkyl, aryl or heteroaryl, preferably H.

In formula (II) $R^8$ is H or alkyl, preferably H or methyl.

In formula (II) $Z^1$ and $Z^2$ are independent from each other O, S, or $NR^{5'}$ preferably both are O.

In formula (II) Y is hydrogen, halogen, alkyl, substituted or unsubstituted cycloalkyl, substituted or unsubstituted E, substituted or unsubstituted O-E, substituted or unsubstituted O-alkylaryl, substituted or unsubstituted O-arylalkyl; in case of said substitution, substitution of one or more hydrogen atoms of the alkyl-, cycloalkyl-, or aryl-groups by halogens are preferred Y can also be

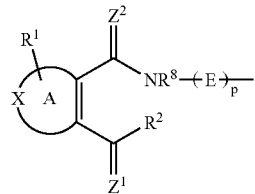

wherein A, X, $R^1$, $R^2$, $R^8$, $Z^1$, $Z^2$ and p have the meaning as defined above. Preferably Y is E and more preferably Y is an optionally substituted phenyl.

In formula (II) E is an alkyl or cycloalkyl group which is optionally substituted by one or more substituents R', or E is a monocyclic or polycyclic substituted or unsubstituted ring system which contains at least one aromatic ring and which may also contain one or more groups X selected from S, O, N, $NR^4$, SO or $SO_2$. In preferred embodiment, E is a monocyclic aromatic ring or an aromatic bicyclic or tricyclic ring system, or cycloalkyl. In case of substitutions of carbon atoms in the ring system, preferably one, two or three carbon atoms are replaced by a group X as defined above.

In formula (II) E is preferably an optionally by one or more substituents R' substituted phenyl, 1-naphtyl, 2-naphthyl, 1-anthracyl and 2-antracyl.

In a preferred embodiment of the present invention in compounds of formula (II) E is an optionally by one or more substituents R' substituted phenyl, or an optionally by one or more substituents R' substituted cycloalkyl.

In formula (II) preferred substituents R' are nitro, halogen, alkoxy, haloalkyl, haloalkyloxy, heteroaryl, alkyl or aryl, more preferably R' is Br, F, Cl, $CF_3$, $OCF_3$, ethoxy or methoxy.

In formula (II) preferred heteroaryl groups are imidazoyl, thienyl, furanyl, pyridyl, pyrimidyl, pyranyl, pyrazolyl, pyrazinyl, thiazolyl, 1H-tetrazol-2-yl, 1H-tetrazol-3-yl, or oxazolyl.

In formula (II) t is preferably 0, 1 or 2.

In formula (a) s is preferably 0 or 1

In the compounds of formula (II) D is O, S, $SO_2$, $NR_4$, or $CH_2$. D is preferably S or more preferably O, when m=1.

In other preferred embodiment, in the compounds of formula (II) m and q are zero and Y is hydrogen, halogen, haloalkyl, haloalkyloxy, alkyl, cycloalkyl or E, preferably F, $CF_3$, $OCF_3$, an optionally by one or more substituents R' substituted phenyl or more preferably an optionally by one or more F, Cl, methoxy, $CF_3$, or $OCF_3$ substituted phenyl.

In formula (II) q is 0 to 10, preferably q is 0, 1 or 2. If q is 1 and n is 0 or 1, D is preferably O (thus m=1).

In particular preferred embodiment of the invention, in compounds of formula (II), q=0, t=1, $Z^1$=O, $Z^2$=O, and A is a thiophen-2,3-dicarboxylic acid monoamide, Y is H or F, or E is phenyl which is either unsubstituted or substituted with Cl, F and/or $CF_3$, $OCH_3$, $OCH_2CH_3$, or $OCF_3$.

In another particularly preferred embodiment of the invention, in compounds of formula (II), q=0, t=1, $Z^1$=O, $Z^2$=O, and A is a thiophen-2,3-dicarboxylic acid monoamide, and E and Y are substituted or unsubstituted phenylene and phenyl, respectively.

In further particularly preferred embodiment, in compounds of formula (II), D=O (thus m=1), $R^3$ is H (thus n=1), q=1, t=1, $Z^1$=O, $Z^2$=O, and E is phenylene which is either unsubstituted or substituted with Cl, P and/or $CF_3$ or $OCF_3$, and Y is phenyl which is also either unsubstituted or substituted with Cl, F and/or $CF_3$, $OCH_3$, $OCH_2CH_3$, or $OCF_3$, and A is a thiophen-2,3-dicarboxylic acid monoamide.

In further particularly preferred embodiment, in compounds of formula (II), D=O (thus m=1), n=0, q=1, t=1, $Z^1$=O, $Z^2$=O, and E is phenylene which is either unsubstituted or substituted with Cl, F and/or $CF_3$ or $OCF_3$, and Y is phenyl which is also either unsubstituted or substituted with Cl, F and/or $CF_3$, $OCH_3$, $OCH_2CH_3$, or $OCF_3$, and A is a thiophen-2,3-dicarboxylic acid monoamide.

In further particularly preferred embodiment, in compounds of formula (II), D=S (thus m=1), n=0, q=1, t=1, $Z^1$=O, $Z^2$=O (thus r=1), and E is phenylene which is either unsubstituted or substituted with Cl, F and/or $CF_3$ or $OCF_3$, and Y is phenyl which is also either unsubstituted or substituted with Cl, F and/or $CF_3$, $OCH_3$, $OCH_2CH_3$, or $OCF_3$, and A is a thiophen-2,3.dicarboxylic acid monoamide.

In particular preferred embodiment of the invention, in compounds of formula (II), q=0, t=1, $Z^1$=O, $Z^2$=O, and A is a furan-3,4-dicarboxylic acid monoamide, Y is H or F, or E is phenyl which is either unsubstituted or substituted with Cl, F and/or $CF_3$, $OCH_3$, $OCH_2CH_3$, or $OCF_3$.

In another particularly preferred embodiment of the invention, in compounds of formula (II), q=0, t=1, $Z^1$=O, $Z^2$=O, and A is a furan-3,4dicarboxylic acid monoamide, and E and Y are substituted or unsubstituted phenylene and phenyl, respectively.

In further particularly preferred embodiment, in compounds of formula (I), D=O (thus m=1), $R^3$ is H (thus n=1), q=1, t=1, $Z^1$=O, $Z^2$=O, and E is phenylene which is either unsubstituted or substituted with Cl, F and/or $CF_3$ or $OCF_3$, and Y is phenyl which is also either unsubstituted or substituted with Cl, F and/or $CF_3$, $OCH_3$, $OCH_2CH_3$, or $OCF_3$, and A is a furan-3,4-dicarboxylic acid monoamide.

In further particularly preferred embodiment, in compounds of formula (II), D=O (thus m=1), n=0, q=1, t=1, $Z^1$=O. $Z^2$=O, and E is phenylene which is either unsubstituted or substituted with Cl, F and/or $CF_3$ or $OCF_3$, and Y is phenyl which is also either unsubstituted or substituted with Cl, F and/or $CF_3$, $OCH_3$, $OCH_2CH_3$, or $OCF_3$, and A is a furan-3,4-dicarboxylic acid monoamide.

In further particularly preferred embodiment, in compounds of formula (II), D=S (thus m=1), n=0, q=1, t=1, $Z^1$=O, $Z^2$=O (thus II), and E is phenylene which is either unsubstituted or substituted with Cl, F and/or $CF_3$ or $OCF_3$, and Y is phenyl which is also either unsubstituted or substituted with Cl, F and/or $CF_3$, $OCH_3$, $OCH_2CH_3$, or $OCF_3$, and A is a furan-3,4-dicarboxylic acid monoamide.

In particular preferred embodiment of the invention, in compounds of formula (II), q=0, t=1, $Z^1$=O, $Z^2$=, and A is a five membered aromatic ring system, wherein one carbon atom is replaced by O, or Y is H or F, and E is phenyl which is either unsubstituted or substituted with Cl, F and/or $CF_3$, $OCH_3$, $OCH_2CH_3$, or $OCF_3$.

In another particularly preferred embodiment of the invention, in compounds of formula (II), q=0, t=1, $Z^1$=O, $Z^2$=O, and A is a five membered aromatic ring system, wherein one carbon atom is replaced by O, or E and Y are substituted or unsubstituted phenylene and phenyl, respectively.

In further particularly preferred embodiment, in compounds of formula (II), D=O (thus m=1), $R^3$ is H (thus n=1), q-1, t=1, $Z^1$=O, $Z^2$=O, and E is phenylene which is either unsubstituted or substituted with Cl, F and/or $CF_3$ or $OCF_3$, and Y is phenyl which is also either unsubstituted or substituted with Cl, F and/or $CF_3$, $OCH_3$, $OCH_2CH_3$, or $OCF_3$, and A is a five membered aromatic ring system, wherein one carbon atom is replaced by O.

In further particularly preferred embodiment, in compounds of formula (II), D=O (thus m=1), n=0, q=1, t=1, $Z^1$=O, $Z^2$=O, and E is phenylene which is either unsubstituted or substituted with Cl, F and/or $CF_3$ or $OCF_3$, and Y is phenyl which is also either unsubstituted or substituted with Cl, F and/or $CF_3$, $OCH_3$, $OCH_2CH_3$, or $OCF_3$, and A is a five membered aromatic ring system, wherein one carbon atom is replaced by O.

In further particularly preferred embodiment, in compounds of formula (II), D=S (thus m=1), n=0, q=1, t=1, $Z^1$=O, $Z^2$=O, and E is phenylene which is either unsubstituted or substituted with Cl, F and/or $CF_3$ or $OCF_3$, and Y is phenyl which is also either unsubstituted or substituted with Cl, F and/or $CF_3$, $OCH_3$, $OCH_2CH_3$, or $OCF_3$, and A is a five membered aromatic ring system, wherein one carbon atom is replaced by O.

In particular preferred embodiment of the invention, in compounds of formula (II), q=0, t=1, $Z^1$=O, $Z^2$=O, and A is a five membered aromatic ring system wherein one carbon atom is replaced by S, or Y is H or F, and E is phenyl which is either unsubstituted or substituted with Cl, F and/or $CF_3$, $OCH_3$, $OCH_2CH_3$, or $OCF_3$.

In another particularly preferred embodiment of the invention, in compounds of formula (II), q=0, t=1, $Z^1$=O, $Z^2$=O, and A is a five membered aromatic ring system, wherein one carbon atom is replaced by S, or E and Y are substituted or unsubstituted phenylene and phenyl, respectively.

In further particularly preferred embodiment, in compounds of formula (II), D=O (thus m=1), $R^3$ is H (thus n=1), q=1, t=1, $Z^1$=O, $Z^2$=O, and E is phenylene which is either unsubstituted or substituted with Cl, F and/or $CF_3$ or $OCF_3$, and Y is phenyl which is also either unsubstituted or substituted with Cl, F and/or $CF_3$, $OCH_3$, $OCH_2CH_3$, or $OCF_3$, and A is a five membered aromatic ring system, wherein one carbon atom is replaced by S.

In further particularly preferred embodiment, in compounds of formula (II), D=O (thus m=1), n=0, q=1, t=1, $Z^1$=O, $Z^2$=O, and E is phenylene which is either unsubstituted or substituted with Cl, F and/or $CF_3$ or $OCF_3$, and Y is phenyl which is also either unsubstituted or substituted with Cl, F and/or $CF_3$, $OCH_3$, $OCH_2CH_3$, or $OCF_3$, and A is a five membered aromatic ring system, wherein one carbon atom is replaced by S.

In further particularly preferred embodiment, in compounds of formula (II), D=S (thus m=1), n=0, q=1, t=1, $Z^1$=O, $Z^2$=O, and E is phenylene which is either unsubstituted or substituted with Cl, F and/or $CF_3$, $OCH_3$, $OCH_2CH_3$, or $OCF_3$, and Y is phenyl which is also either unsubstituted or substituted with Cl, F and/or $CF_3$ or $OCF_3$, and A is a five membered aromatic ring system, wherein one carbon atom is replaced by S.

In further particularly preferred embodiment, in compounds of formula (II), $Z^1$=O (thus r=1), $Z^2$=O, q=0, t=1, $R^2$=O, $R^8$=H and E is phenylene which is either unsubstituted or substituted with Cl, F and or $CF_3$, $OCH_3$, $OCH_2CH_3$, or $OCF_3$, and Y is phenyl which is also either unsubstituted or substituted with Cl, F and/or $CF_3$, $OCH_3$, $OCH_2CH_3$, or $OCF_3$, and A is a five membered aromatic ring system, wherein one carbon atom is replaced by S.

In further particularly preferred embodiment, in compounds of formula (II), $Z^1$=O, $Z^2$=O, q=0 or 1, t=2, E is phenylene which is either unsubstituted or substituted with Cl, F and/or $CF_3$, $OCH_3$, $OCH_2CH_3$, or $OCF_3$, and Y is phenyl which is also either unsubstituted or substituted with Cl, F and/or $CF_3$ or $OCF_3$, and $R^2$ together with the nitrogen atom which is attached to $R^8$ form a 6 membered heterocyclic ring with the proviso that $R^2$ is —$[CH_2]_8$ and $R^8$ is absent; and A is furan.

In further particularly preferred embodiment in compounds of formula (II), $Z^1$=O, $Z^2$=O, q=0 or 1, t=2, E is phenylene which is either unsubstituted or substituted with Cl, F and/or $CF_3$, $OCH_3$, $OCH_2CH_3$, or $OCF_3$, and Y is H or F, and $R^2$ togehter with the nitrogen atom which is attached to $R^8$ form a 6 membered heterocyclic ring with the proviso that $R^2$ is —$[CH_2]_8$ and $R^8$ is absent; and A is furan.

The compounds of formula (II) to be used according to the invention can form salts with inorganic or organic acids or bases. Examples of such salts are, for example, alkali metal salts, in particular sodium and potassium salts, or ammonium salts.

The compounds of the present invention can be used for a variety of human and animal diseases, preferably human diseases, where inhibition of the pyrimidine metabolism is beneficial. Such diseases are:

fibrosis, uveitis, rhinitis, asthma or athropathy, in particular, arthrosis all forms of rheumatism acute immunological events and disorders such as sepsis, septic shock, endotoxic shock, Gram-negative sepsis, toxic shock syndrome, acute respiratory distress syndrome, stroke, reperfusion injury, CNS injury, serious forms of allergy, graft versus host and host versus graft reactions, alzheimer's or pyresis, restenosis, chronic pulmonary inflammatory disease, silicosis, pulmonary sarcosis, bone resorption disease. These immunological events also include a desired modulation and suppression of the immune system;

all types of autoimmune diseases, in particular rheumatoid arthritis, rheumatoid spondylitis, osteoarthritis, gouty arthritis, multiple sclerosis, insulin dependent diabetes mellitus and non-insulin dependent diabetes, and lupus erythematoidis, ulcerative colitis, Morbus Crohn, inflammatory bowel disease, as well as other chronic inflammations, chronic diarrhea;

dermatological disorders such as psoriasis progressive retinal atrophy all kinds of infections including opportunistic infections.

The compounds according to the invention and medicaments prepared therewith are generally useful for the treatment of cell proliferation disorders, for the treatment or prophylaxis, immunological diseases and conditions (as for instance inflammatory diseases, neuroimmunological diseases, autoimmune diseases or other).

The compounds of the present invention are also useful for the development of immunomodulatory and anti-inflammatory medicaments or, more generally, for the treatment of diseases where the inhibition of the pyrimidine biosynthesis is beneficial.

The compounds of the present invention are also useful for the treatment of diseases which are cause by malignant cell proliferation, such as all forms of hematological and solid cancer. Therefore the compounds according to the invention and medicaments prepared therewith are generally useful for regulating cell activation, cell proliferation, cell survival, cell differentiation, cell cycle, cell maturation and cell death or to induce systemic changes in metabolism such as changes in sugar, lipid or protein metabolism. They can also be used to support cell generation poiesis, including blood cell growth and generation (prohematopoietic effect) after depletion or destruction of cells, as caused by, for example, toxic agents, radiation, immunotherapy, growth defects, malnutrition, malabsorption, immune dysregulation, anemia and the like or to provide a therapeutic control of tissue generation and degradation, and therapeutic modification of cell and tissue maintenance and blood cell homeostasis.

These diseases and conditions include but are not limited to cancer as hematological (e.g. leukemia, lymphoma, mycloma) or solid tumors (for example breast, prostate, liver, bladder, lung, esophageal, stomach, colorectal, genitourinary, gastrointestinal, skirt, pancreatic, brain, uterine, colon, head and neck, and ovarian, melanoma, astocytoma, small cell lung cancer, glioma, basal and squameous cell carcinoma, sarcomas as Kaposi's sarcoma and osteosarcoma), treatment of disorders involving T-cells such as aplastic anemia and DiGeorge syndrome, Graves' disease Leflunomide, was previously found to inhibit HCMV replication in cell culture. Ocular herpes is the most common couse of infectious blindness in the developed world. There are about 50,000 cases per year in the US alone, of which 90% are recurences of initial infections. Recurrences arm treated with antivirals and cordcosteroids. Cytomegalovirus another herpes virus is a common couse of retinal damage and blindness in patients with aids. The compounds of the present invention can be used alone or in combination with other antiviral compounds such as Ganciclovir and Foscarnet to treat such diseases.

The compounds of the present invention can further be used for diseases that are caused by protozoa infestations in humans and animals. Such veterinary and human pathogenic protozoas are preferably intracellular active parasites of the phylum Apicomplexa or Samcomastigophora, especially Trypanosoma, Plasmodia, Leishmania, Babesia and Theileria, Cryptosporidia, Sacrocystida, Amoebia, Coccidia and Trichomonadia. These active substances or corresponding drugs are especially suitable for the treatment of Malaria tropical caused by *Plasmodium faociparum,* Malaria tertiana, caused by *Plasmodium vivax* or *Plasmodium ovate* and for the treatment of Malaria quana caused by *Plasmodium malariae.* They are also suitable for the treatment of Toxoplasmnosis, caused by *Toxoplasma gondii,* Coccidiosis, caused for instance by *Isospora belli,* intestinal Sarcosporidiosis, caused by *Sarcocystis suihominis,* dysentery caused by *Entamoeba histolytica,* Cryptosporidiosis, caused by *Cryptosporidium parvum,* Chargas' disease, caused by *Trypanosoma cruzi,* sleeping sickness, caused by *Trypanosoma brucei rhodesiense* or *gambiense,* the cutaneous and visceral as well as other forms of Leishmaniosis. They are also suitable for the treatment of animals infected by veterinary pathogenic protozoa, like *Theileria parva,* the pathogen causing bovine East coast fever, *Trypanosoma congolense congolense* or *Trypanosoma vivax vivax, Trypanosoma brucei brucei,* pathogens causing Nagana cattle disease in Africa, *Trypanosoma brucei evansi* causing Surra, *Babesia bigemina,* the pathogen causing Texas fever in cattle and buffalos, *Babesia bovis,* the pathogen causing european bovine Babesiosis as well as Babesiosis in dogs, cats and sheep, *Sarcocystis ovicanis* and *ovifelis* pathogens causing Sarcocystiosis in sheep, cattle and pigs, Cryptosporidia, pathogens causing Cryptosporidioses in cattle and birds, Eimeria and Isospora species, pathogens causing Coccidiosis in rabbits, cattle, sheep, goats, pigs and birds, especially in chickens and turkeys. The use of the compounds of the present invention is preferred in particular for the treatment of Coccidiosis or Malaria infections, or for the preparation of a drug or feed stuff for the treatment of these diseases.

This treatment can be prophylactic or curative. In the treatment of malaria, the compounds of the present invention may be combined with other anti-malaria agents.

The compounds of the present invention can further be used for viral infections or other infections caused for instance by *Pneumocystis carinii.*

The compounds of formula (II) and their pharmacologically acceptable salts can be administered to animals, preferably to mammals, and in particular to humans, dogs and chickens as therapeutics per se, as mixtures with one another or in the form of pharmaceutical preparations which allow enteral or parenteral use and which as active constituent contain an effective dose of at least one compound of formula (II), or a salt thereof, in addition to customary pharmaceutically innocuous excipients and additives. The compounds of formula (II) can also be administered in form of their salts, which are obtainable by reacting the respective compounds with physiologically acceptable acids and bases.

The therapeutics can be administered orally, e.g. in the form of pills, tablets, coated tablets, sugar coated tablets, hard and soft gelatin capsules, solutions, syrups, emulsions or suspensions or as aerosol mixtures. Administration, however, can also be carried out rectally, e.g. in the form of suppositories, or parenterally, e.g. in the form of injections or infusions, or percutaneously, e.g. in the form of ointments, creams or tinctures.

In addition to the active compounds of formula (II) the pharmaceutical composition can contain further customary, usually inert carrier materials or excipients. Thus, the pharmaceutical preparations can also contain additives, such as, for example, fillers, extenders, disintegrants, binders, glidants, wetting agents, stabilizers, emulsifiers, preservatives, sweetening agents, colorants, flavorings or aromatizers, buffer substances, and furthermore solvents or solubilizers or agents for achieving a depot effect, as well as salts for changing the osmotic pressure, coating agents or antioxidants. They can also contain two or more compounds of formula (II) or their pharmacologically acceptable salts and also other therapeutically active substances.

Thus, the compounds of the present invention can be used in the form of one substance alone or in combination with other active compounds—for example with medicaments already known for the treatment of the aforementioned diseases, whereby in the latter case a favorable additive, amplifying effect is noticed. Suitable amounts to be administered to humans range from 5 to 500 mg.

To prepare the pharmaceutical preparations, pharmaceutically inert inorganic or organic excipients can be used. To prepare pills, tablets, coated tablets and hard gelatin capsules, for example, lactose, corn starch or derivatives thereof, talc, stearic acid or its salts, etc. can be used. Excipients for soft gelatin capsules and suppositories are, for example, fats, waxes, semi-solid and liquid polyols, natural or hardened oils etc. Suitable excipients for the production of solutions and syrups are, for example, water, sucrose, invert sugar, glucose, polyols etc. Suitable excipients for the production of injection solutions are, for example, water, alcohols, glycerol, polyols or vegetable oils.

The dose can vary within wide limits and is to be suited to the individual conditions in each individual case. For the above uses the appropriate dosage will vary depending on the mode of administration, the particular condition to be treated and the effect desired. In general, however, satisfactory results are achieved at dosage rates of about 1 to 100 mg/kg animal body weight preferably 1 to 50 mg/kg. Suitable dosage rates for larger mammals, for example humans, are of the order of from about 10 mg to 3 g/day, conveniently administered once, in divided doses 2 to 4 times a day, or in sustained release form.

In general, a daily dose of approximately 10 mg to 5000 mg, preferably 50 to 500 mg, per human individual is appropriate in the case of the oral administration which is the preferred form of administration according to the invention. In the case of other administration forms too, the daily dose is in similar ranges.

The compounds of formula (II) can also be used in the form of a precursor prodrug) or a suitably modified form, that releases the active compound in vivo. Such precursors such as the preferred embodiments of $R^6$ or $R^1$ can be obtained for example by masking the free acid group with an ester group, which is then in turn transformed into the free acid group in vivo [F. W. Sum et al. Bioorg. & Med. Chem. Lett. 9 (1999), 1921-1926; Ada Rephaeli et. al. Drug Development Research 50 (2000) 379-391; H. Ishikawa, Current Med. Chem. 6 (1999), 575-597]. Further precursors for the preferred embodiment of $R^6$ or $R^1$ is tetrazole, another metabolism-resistant isosteric replacements for the carboxylic acid group as described by J. Herr, Bioorg. & Med. Chem. Lett. 10 (2002), 3379-3393. Other precursors for the preferred embodiments of $R^5$ can be obtained for example by masking the amidine with an hydroxy group, which is then in turn transformed into the free amidine in vivo [R. M. Scarborough, J. Med. Chem. 43, 19, (2000), 3454-3473].

EXAMPLES

Method A

General Method for Synthesis of 5-membered Heteroaromatic 2,3-dicarboxylic acide mono amide Derivative The biphenyl-derivative was dissolved under inert atmosphere in dry dichloromethane. Triethylamine (1.2 Equ) was added in one portion. Freshly prepared thiophene-3-carbonyl chloride (1.2 Equ) or furan-3-carbonylchloride (1.2 Equ) or the respective heteroaromatic 2'-carbonyl chloride solved in dichloromethane was added drop wise. After addition the mixture was heated at 45° C. for 4 h. The solvent was removed by vacuum. The amide was solved in tetrahydrofuran and cooled to −78° C. Butyl lithium (2 equ) was added during 15 minutes and the mixture was stirred at −78° C. for 30 minutes. Solid carbon dioxide was added in one portion and the mixture was allowed to warm to room temperature within 4 h. The reaction was quenched with 2 n HCl extracted 3 times with ethyl acetate, the combined organic layers were washed with sodium bicarbonate and brine, dried over MgSO4 and filtered. The solvent was removed by vacuum. The material was purified by HPLC (using a water/acetonitrile gradient) to yield the pure product.

Method C

General Method for the 5-membered Hetero Aromatic 3,4-carboxylic acid mono amide Derivatives Thiophene-3,4-dicarboxylic acid or furan-3,4-dicarboxylic acide was suspended in acetic acid anhydride and heated at 100° C. for 3 h. The reaction solution was cooled to room temperature. The solvent was removed by vacuum. It was dried for 6 h to give the anhydride in quantitative yield. The resulting anhydride was solved in dichloromethane (0.36 mmol/ml). To this solution of the biphenyl amine (1 equ) derivative was added and the reaction mixture was heated at 45° C. for 12 h. The solvent was removed by vacuum. The product was purified by HPLC. Yields are between 30 and 70%

Example 1

3-(Biphenyl-4-ylcarbamoyl)-thiophene-2-carboxylic acid synthesized by method A, $^1$H-NMR: δ=1.25 ($m_c$, 9 H. $CH_3$), 3.17 ($m_c$, 6 H, $CH_2$), 7.12-7.83 (m, 9 H, $CH_{Ar}$), 7.26 ($m_c$, 1 H, CH), 7.62 ($m_c$, 1 H, CH), 14.88 (s, 1 H, NH). LC/(+)-ESI-MS: m/z=324 $[M+H]^+$ Example 2

3-(2'-Ethoxy-3,5-difluoro-biphenyl-4-ylcarbamoyl)-thiophene-2-carboxylic acid synthesized by method A, $^1$H-NMR: δ=1.22 ($m_c$ 12 H, $CH_3$) 3.12 ($m_c$, 6 H, $CH_2$), 3.99 ($m_c$, 2 H, $CH_2$), 6.87-7.30 (m, 6 H, $CH_{Ar}$), 7.27 ($m_c$, 1 H, CH), 7.58 ($m_c$, 1 H, CH), 14.47 (s, 1 H, NH). LC/(+)-ESI-MS: m/z=404 $[M+H]^+$ Example 3

3-(3'-Ethoxy-3,5-difluoro-biphenyl-4-ylcarbamoyl)-thiophene-2-carboxylic acid synthesized by method A, $^1$H-NMR: δ=1.21 ($m_c$, 9 H, $CH_3$) 1.27 ($m_c$,3 H, $CH_3$) 3.11 ($m_c$, 6 H, $CH_2$), 4.03 ($m_c$, 2 H, $CH_2$), 6.81-7.25 (m, 6 H, $CH_{Ar}$), 7.26 ($m_c$, 1 H, CH), 7.57 ($m_c$, 1 H, CH), 14.44 (s, 1 H, NH). LC/(+)-ESI-MS: m/z=404 $[M+H]^+$ Example 4

3-(3,5-difluoro-2',4'-dimethoxy-biphenyl-4-ylcarbamoyl)-thiophene-2-carboxylic acid synthesized by method A, $^1$H-NMR: δ=1.21 ($m_c$, 9 H, $CH_3$), 3.09 ($m_c$, 6 H, $CH_2$), 3.73 (s, 3 H, $CH_3$), 3.74 (s, 3 H, $CH_3$), 6.48-7.24 (m, 5 H, $CH_{Ar}$), 7.26 ($m_c$, 1 H, CH ), 7.57 ($m_c$, 1 H, CH), 14.44 (s, 1 H, NH), LC/(+)-ESI-MS: m/z=420 $[M+H]^+$ Example 5

3-(2,3,5,6-Tetrafluoro-2'-methoxy-biphenyl-4-ylcarbamoyl)-thiophene-2-carboxylic acid synthesized by method A, ¹H-NMR: δ=1.23 (m$_c$, 9 H, CH$_3$), 3.14 (m$_c$, 6 H, CH$_2$), 3.72 (s, 3 H, CH$_3$), 6.94-7.42 (m, H, CH$_{Ar}$), 7.31 (m$_c$, 1 H, CH), 7.59 (m$_c$, 1 H, CH), 14.67 (s, 1 H, NH). LC/(+)-ESI-MS: m/z=426 [M+H]$^+$

Example 6

3-(2'-Chloro-3,5-difluoro-biphenyl-4-ylcarbamoyl)-thiophene-2-carboxylic acid synthesized by method A, ¹H-NMR: δ=1.21 (m$_c$, 9 H, CH$_3$), 3.08 (m$_c$, 6 H, CH$_2$), 6.99-7.54 (m, 6 H, CH$_{Ar}$), 7.28 (m$_c$, 1 H, CH), 7.59 (m$_c$, 1 H, CH), 14.67 (s, 1 H, NH). LC/(+)-ESI-MS: m/z=394 [M+H]$^+$

Example 7

3-(3,5,2'-Trifluoro-biphenyl-4-ylcarbamoyl)-thiophene-2-carboxylic acid synthesized by method A, ¹H-NMR: δ=1.22 (m$_c$, 9 H, CH$_3$), 3.11 (m, 6 H, CH$_2$), 7.01-7.54 (m, 6 H, CH$_{Ar}$), 7.27 (m$_c$, 1 H, CH), 7.58 (m$_c$, 1 H, CH), 14.74 (s, 1 H, NH). LC/(+)-ESI-MS: m/z=378 [M+H]$^+$

Example 8

3-(2-Chloro-2'-methoxy-biphenyl-4-ylcarbamoyl)-thiophene-2-carboxylic acid synthesized by method A, ¹H-NMR: δ=1.26 (m$_c$, 9 H, CH$_3$) 3.17 (m$_c$, 6 H, CH$_2$), 6.82-8.01 (m, 7 H. CH$_{Ar}$), 7.26 (m$_c$, 1 H, CH), 7.61 (m$_c$, 1 H, CH), 15.1 (s, 1 H, NH). LC/(+)-ESI-MS: m/z=388 [M+H]$^+$

Example 9

3-(2,3,5,6-Tetrafluoro-3'-trifluoromethoxy-biphenyl-4-ylcarbamoyl)-thiophene-2-carboxylic acid synthesized by method A, LC/(+)-ESI-MS: m/z=480 [M+H]$^+$

Example 10

3-(3-Fluoro-3'-methoxy-biphenyl-4-ylcarbamoyl)-thiophene-2-carboxylic acid synthesized by method A, ¹H-NMR: δ=3.75 (s, 3 H, CH$_3$), 6.79-7.47 (m, 6 H, CH$_{Ar}$), 7.77 (m$_c$, 2 H, CH), 8.20 (m$_c$, 1 H, CH$_{Ar}$), 11.10 (s, 1 H, NH). LC/(+)-ESI-MS: m/z=372 [M+H]$^+$

Example 11

3-(3,5-Difluoro-3'-trifluoromethoxy-biphenyl-4-ylcarbamoyl)-thiophene-2-carboxylic acid synthesized by method A, ¹H-NMR: δ=1.22 (m$_c$, 9 H, CH$_3$), 3.13 (m$_c$, 6 H, CH$_2$), 7.22-7.68 (m, 6 H, CH$_{Ar}$), 7.27 (m$_c$, 1 H, CH), 7.57 (m$_c$, 1 H, CH), 14.67 (s, 1 H, NH). LC/(+)-ESI-MS: m/z=444 [M+H]$^+$

Example 12

3-(Biphenyl4-ylcarbamoyl)-furan-2-carboxylic acid synthesized by method A, LC/(+)ESI-MS: m/z=308 [M+H]$^+$

Example 13

4-(Biphenyl-4-ylcarbamoyl)-thiophene-3-carboxylic acid synthesized by method C, ¹H-NMR: δ=7.24-8.0 (m, 9 H, CH$_{Ar}$), 8.47 (m$_c$, 2 H, CH). LC/(+)-ESI-MS: m/z=324 [M+H]$^+$

Example 14

4-(2-Chloro-2'-methoxy-biphenyl-4-ylcarbamoyl)-thiophene-3-carboxylic acid synthesized by method C, ¹H-NMR: δ=3.76 (s, 3 H, CH$_3$), 6.97-8.14 (m, 7 H, CH$_{Ar}$), 8.40-8.55 (m, 2 H, CH), 11.92 (s, 1 H, NH). LC/(+)-ESI-MS: m/z=388 [M+H]$^+$

Example 15

4-(3,5,2'-Trifluoro-biphenyl-4-ylcarbamoyl)-thiophene-3-carboxylic acid synthesized by method C, ¹H-NMR: δ=7.23-7.69 (m, 6 H, CH$_{Ar}$), 8.56 (m$_c$, 2 H, CH), 11.54 (s, 1 H. 1 NH). LC/(+)-ESI-MS: m/z=378 [M+H]$^+$

Example 16

4-(3'-Ethoxy-3,5-difluoro-biphenyl-4-ylcarbamoyl)-thiophene-3-carboxylic acid synthesized by method C, ¹H-NMR: δ=1.40 (m$_c$, 3 H, CH$_3$), 4.17(m$_c$, 2 H, CH$_2$), 6.94-7.50 (m, 6 H, CH$_{Ar}$), 8.58 (m$_c$, 2 H, CH). LC/(+)-ESI-MS: m/z 404 [M+H]$^+$

Example 17

4-(2'-Ethoxy-3,5-difluoro-biphenyl-4-ylcarbamoyl)-thiophene-3-carboxylic acid synthesized by method C, ¹H-NMR: δ=1.37 (m$_c$, 3 H, CH$_3$), 4.14 (m$_c$, 2 H, CH$_2$), 7.01-7.47 (m, 6 H, CH$_{Ar}$), 8.58 (m$_c$, 2 H, CH). LC/(+)-ESI-MS: m/z 404 [M+H]$^+$

Example 18

4-(3,5-Difluoro-3'-trifluoromethoxy-biphenyl-4-ylcarbamoyl)-thiophene-3-carboxylic acid synthesized by method C, ¹H-NMR: δ=7.37-8.4 (m, 6 H CH$_{Ar}$), 8.58 (m$_c$, 2 H, CH). LC/(+)-ESI-MS: m/z=444 [M+H]$^+$

Example 19

4-(3-Fluoro-3'-methoxy-biphenyl-4-ylcarbamoyl)-thiophene-3-carboxylic acid synthesized by method C, LC/(+)-ESI-MS: m/z=372 [M+H]$^+$

Example 20

4-(Biphenyl4-ylcarbamoyl)-furan-3-carboxylic acid synthesized by method C, LC/(+)-ESI-MS: m/z=308 [M+H]$^+$

Example 21

2-(Biphenyl-4-ylcarbamoyl)-thiophene-3-carboxylic acid synthesized by method A, LC/(+)-ESI-MS: m/z=324 [M+H]$^+$

Example 22

2-(Biphenyl-4-ylcarbamoyl)-furan-3-carboxylic acid synthesized by method A, LC/(+)-ESI-MS: m/z=308 [M+H]$^+$ 3. Inhibition Assay of DHODH Activity The standard assay mixture contained 50 μM decyclo ubichinone, 100 μM dihydroorotate, 60 μM 2,6-dichloroindophenol, as well as 20 mU DHODH. The volume activity of the recombinant enzyme used was 30 U/ml. Measurements were conducted in 50 mM TisHCl (150 mM KCl, 0.1% Triton X-100, pH 8.0) at 30° C. in a fial volume of 1 ml. The components were mixed, and the reaction was started by adding dihydroorotate. The course of reaction was followed by spectrophotometrically measuring the decrease in absorption at 600 nm for 2 min.

Inhibitory studies were conducted in a standard assay with additional variable amounts of inhibitor. For the determination of the $IC_{50}$ values (concentration of inhibitor required for 50% inhibition) at least five different inhibitor concentrations were applied.

These investigations were carried out with recombinant human as well as with recombinant murine DHODH provided by Prof. M. Löffler, Marburg, Germany [M. Löffler, Chem. Biol. Interact 124, (2000), 61-76].

As a reference the active metabolite of leflunomide A77-1726 was used [J. Jöckel et. al. Biochemical Pharmacology 56 (1998), 1053-1060].

Examples 1, 2, 3, 4, 5, 6, 7, 8, 10, 11, 14, 15, 16, 17, 18, 19, 21, 13, 12, 22, 20 showed an inhibition of the human DHODH <1 µl Examples 9, 21 showed an inhibition of the human DHODH between 1 and 5 µl

What is claimed is:

1. A compound of the general formula (II) and salts and physiologically functional derivatives thereof,

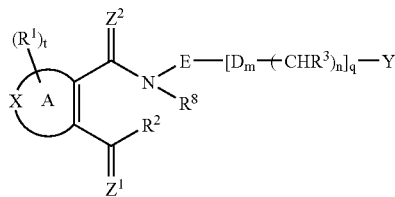

wherein
A is a heteroaromatic 5-membered ring system containing one or more groups X selected from the group consisting of S, O, N, $NR^4$, $SO_2$ and SO;
D is O, S, $SO_2$, $NR^4$, or $CH_2$;
$Z^1$ and $Z^2$ are independent from each other O, S, or $NR^5$;
$R^1$ independently represents H, halogen, haloalkyl, haloalkyloxy —$CO_2R"$, —$SO_3H$, —OH, —CONR*R", —CR"O, —$SO_2$—NR*R", —$NO_2$, —$SO_2$—R", —SO—R*, —CN, alkoxy, alkylthio, aryl, —NR"—$CO_2$—R'; —NR"—CO—R*, —NR"—$SO_2$—R', —O—CO—R*, —O—$CO_2$—R*, —O—CO—NR*R"; cycloalkyl, alkylamino, hydroxyalkylamino, —SH, heteroaryl, or alkyl;
R* independently represents H, alkyl, cycloalkyl, aminoalkyl, alkoxy, —OH, —SH, alkylthio, hydroxyalkyl, haloalkyl, haloalkyloxy, aryl or heteroaryl;
R' independently represents H, —$CO_2R"$, —CONHR", —CR"O, —$SO_2NR"$, —NR"—CO-haloalkyl, —$NO_2$, —NR"—$SO_2$-haloalkyl, —NR"—$SO_2$-alkyl, —$SO_2$-alkyl, —NR"—CO-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkyloxy, aryl, arylalkyl or heteroaryl;
R" independently represents hydrogen, haloalkyl, hydroxyalkyl, alkyl, cycloalkyl, aryl, heteroaryl or aminoalkyl;
$R^2$ is H or $OR^6$;
$R^3$ is H, alkyl, cycloalkyl, aryl, alkoxy, O-aryl; O-cycloalkyl, halogen, aminoalkyl, alkylamino, hydroxylamino, hydroxylalkyl, halo alkyloxy, heteroaryl, alkylthio, S-aryl; S-cycloalkyl, arylalkyl, or haloalkyl;
$R^4$ is H, alkyl, cycloalkyl, aryl or heteroaryl;
$R^5$ is H, OH, alkoxy, O-aryl, alkyl or aryl;
$R^6$ is H, alkyl, cycloalkyl, aryl, arylalkyl, heteroaryl, alkylaryl, alkoxyalkyl, acylmethyl, (acyloxy)alkyl, non-symmetrical (acyloxy)alkyldiester, or dialkyiphosphate;
$R^7$ is H, OH, alkyl, aryl, alkoxy, O-aryl, cycloalkyl, or O-cycloalkyl; $R^8$ is R hydrogen, or alkyl;
E is a monocyclic or polycyclic substituted or unsubstituted ring system which contains at least one aromatic ring and which may also contain one or more groups X selected form S, O, N, $NR^4$, SO, or $SO_2$;
Y is a phenyl substituted by one or more substituents R';
m is 0 or 1;
n is 0 or 1;
p is 0 or 1;
q is 0 or 1;
s is 0 to 2; and
t is 0 to 3;
with the proviso that the following compounds are excluded:
compounds wherein ring A contains five atoms, $Z^1=Z^2=O$, and $R^2$ together with the nitrogen atom which is attached to $R^8$ forms a 5 membered heteroyclic ring with the proviso that $R^2$ is—$[CH_2]_8$, $R^8$ is absent and s is 0;
compounds wherein ring A contains three carbon atoms and two nitrogen atoms, $Z^1=Z^2=O$, and $R^2$ together with the nitrogen atom which is attached to $R^8$ form a 5 membered heteroyclic ring with the proviso that $R^2$ is —$[CH_2]_8$, $R^8$ is absent and s is 0;
4-[4-(naphthalin-2-yl) thiazol-2-ylaminocarbonyl]-furan-3-carboxylic acid; and
5-[4-(naphthalin-2-yl) thiazol-2-ylaminocarbonyl]-2H-[1,2,3]-triazole-4-carboxylic acid.

2. The compound according to claim 1, with the proviso that the following compounds are addition excluded:
2-[4-(naphthalin-2-yl)thiazol-2-ylaminocarbonyl] thiophene-3-carboxylic acid;
3-[4-(naphthalin-2-yl)thiazol-2-ylaminocarbonyl] thiophene-2-carboxylic acid.

3. A pharmaceutical composition comprising a compound as defined in claim 1 in free form or in the form of a pharmaceutically acceptable salt or physiologically functional derivative and a pharmaceutically acceptable diluent or carrier.

4. A medicament comprising a compound according to claim 1.

5. A method of inhibiting dihydrooratate dehydrogenase for treating a disease or indication selected from the group consisting of rheumatism, diseases that are caused by viral infections and *Pneumocystis carinii*, fibrosis, uveitis, rhinitis, asthma, athropathy, multiple sclerosis, ulcerative colitis, Morbus Crohn, inflammatory bowel disease and psoriasis comprising administering to a patient in need thereof an effective amount of a compound as defined in claim 1 or a physiologically functional derivative or a pharmacologically tolerable salt thereof.

6. A process for the preparation of a compound as defined in claim 1, wherein if the compound is a 5-membered heteroaromatic 2,3-dicarboxylic acid mono amide derivative and X is O or S, said process comprising:
a) the amidation of a thiophene-3-carboxyl chloride derivative or thiophene-2-carboxyl chloride derivative or a respective furan derivative with an amine

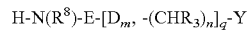

wherein $R^8$, E, D, m, $R^3$, n, q and Y are as specified in claim 1; and b) the directed ortho-metalation with butyl lithium and scavenging of the resulting anion with solid carbon dioxide; or wherein the compound is a 5-membered heteroaromatic 3,4-dicarboxylic acid mono amide derivative and X is O or S, said process comprising:

a) the formation of an anhydride of thiophene-3,4-dicarboxylic acid derivative or furan-3,4-dicarboxylic acid derivative, using acetic acid anhydride; and b) the subsequent conversion of the anhydride to the corresponding mono-amide using an amine derivative of the general formula $$H-N(R^8)-E-[D_m, -(CHR_3)_n]_q-Y$$

wherein $R^8$, E, D, m, $R^3$, n, q and Y are as specified in claim 1.

7. The compound of claim 1, wherein Y is a phenyl substituted by one or more sub stituents R', the R' substitutents selected from the group consisting of F, Cl, methoxy, $CF_3$, and $OCF_3$.

* * * * *